(12) United States Patent
Jägle

(10) Patent No.: US 7,648,095 B2
(45) Date of Patent: Jan. 19, 2010

(54) AGITATING OR DISPERSING APPARATUS

(75) Inventor: Peter Jägle, Dottingen (DE)

(73) Assignee: IKA - Werke GmbH & Co. KG, Staufen (DE)

( * ) Notice: Subject to any disclaimer, the term of this patent is extended or adjusted under 35 U.S.C. 154(b) by 635 days.

(21) Appl. No.: 11/414,828

(22) Filed: May 1, 2006

(65) Prior Publication Data

US 2006/0245298 A1    Nov. 2, 2006

(30) Foreign Application Priority Data

Apr. 29, 2005   (DE) .................. 10 2005 020 460

(51) Int. Cl.
B02C 17/00 (2006.01)
B02C 23/02 (2006.01)
(52) U.S. Cl. .................. 241/172; 241/199.12; 366/279
(58) Field of Classification Search ................ 241/172, 241/199.12; 366/279, 331
See application file for complete search history.

(56) References Cited

U.S. PATENT DOCUMENTS

| | | | | |
|---|---|---|---|---|
| 1,675,694 A * | 7/1928 | Claybourn | ............. | 241/199.12 |
| 2,203,089 A * | 6/1940 | Hollenback | ............. | 241/199.12 |
| 2,203,404 A * | 6/1940 | Chace | ............. | 241/199.12 |
| 3,636,753 A * | 1/1972 | Thiele et al. | ............. | 73/54.25 |
| 4,637,555 A * | 1/1987 | Furuichi et al. | ............. | 241/46.02 |
| 2002/1011920 | 8/2002 | Haskell | ............. | 424/489 |
| 2004/0155132 A1 * | 8/2004 | McPherson et al. | .... | 241/199.12 |
| 2005/0023386 A1 | 2/2005 | Haskell | ............. | 241/16 |
| 2006/0013064 A1 | 1/2006 | Bucher | ............. | 366/303 |

FOREIGN PATENT DOCUMENTS

| | | |
|---|---|---|
| DE | 15 57 186 | 3/1972 |
| DE | 2 118 897 | 11/1972 |
| DE | 24 40 079 | 3/1975 |
| DE | 197 05 118 A1 | 8/1998 |
| EP | 0 409 039 A1 | 1/1991 |
| FR | 2 289 094 | 5/1976 |
| GB | 1 464 733 | 2/1977 |
| JP | 60-166024 | 8/1985 |
| WO | WO 2004/035191 A1 | 4/2004 |

OTHER PUBLICATIONS

International Search Report (PCT/EP2006/003801).
International Search Report (PCT/EP2006/003920).

* cited by examiner

*Primary Examiner*—Bena Miller
(74) *Attorney, Agent, or Firm*—K&L Gates LLP

(57) ABSTRACT

An agitating or dispersing apparatus (1) with a hermetically sealed mixing chamber (5), an agitating or dispersing tool (2) that can be driven in this mixing chamber (5) about a central axis and with a rod-shaped element (3) for transferring the power of a drive (4) onto this tool (2), and with the drive (4) located outside of the mixing chamber (5). The rod-shaped element (3) is connected at the entrance into the mixing chamber (5) to a membrane (6) that is part of a wall (7) of the mixing chamber (5), and the rod-shaped element (3) can be put in a wobbling motion by the drive (4) so that its end inside the mixing chamber (5) executes a circular motion. The end of the rod-shaped element (3) located in the mixing chamber (5) attacks the tool (2) eccentrically to its axis of rotation.

20 Claims, 4 Drawing Sheets

AGITATING OR DISPERSING APPARATUS

CROSS-REFERENCES TO RELATED APPLICATIONS

This application claims the benefit of German patent application 10 2005 020 460.0-23, filed Apr. 29, 2005, herein incorporated by reference.

BACKGROUND OF THE INVENTION

The invention relates to an agitating or dispersing apparatus with a hermetically sealed mixing chamber, an agitating or dispersing tool that can be driven in this mixing chamber about a central axis and with a rod-shaped element for transferring the power of a drive onto this tool, and with such a drive located outside of the mixing chamber.

Such agitating or dispersing apparatuses are known in many forms. As rule a shaft is provided as a rod-shaped transfer element for the drive of a drive motor onto the tool, which shaft runs through a wall, e.g., the bottom or also the top of the mixing chamber and is connected to the tool located inside the mixing chamber.

Therefore, the tool can be driven in an advantageous manner via an approximately concentric and coaxial shaft. However, this drive axle or drive shaft must run through the wall of the mixing chamber and the better it is sealed the less the contents of the mixing chamber will exit to the outside. The working of poisonous or contaminated mixing materials such as those that occur in medicine (e.g., in the form of tissue or the like) is especially critical.

It can simply not be excluded in the case of customary sealing devices that corresponding sealing rings are worn to such an extent, at least after a certain running time, that slight and hardly perceivable amounts might be able to pass through that are either directly dangerous for the user if very poisonous, or that necessitate a correspondingly great amount of work after the actual agitating, mixing and dispersing process due to the contamination of the environment.

There is therefore the problem of creating an apparatus of the initially defined type in which an exiting of mixing material in the area of the drive is excluded.

SUMMARY OF THE INVENTION

In order to solve this problem, the invention provides that the rod-shaped element is connected at the entrance into the mixing chamber to a membrane that is part of a wall of the mixing chamber, that the rod-shaped element can be put in a wobbling motion by the drive so that its area inside the mixing chamber and in particular its end located there execute a circular motion, and that the end of the rod-shaped element, which end is located in the mixing chamber, attacks the agitating or dispersing tool eccentrically to its axis of rotation. Thus, the membrane makes possible the movement of the rod-shaped element in its deflection without the latter having to rotate about its own axis, and sealing rings or similar sealing elements are not necessary in the area of the entrance of this rod-shaped element into the mixing chamber and therefore will not become leaky. Rather, a hermetically tight mixing chamber results in spite of the entrance of a drive element in which mixing chamber the tool can nevertheless be mechanically caused to rotate by this drive element.

The rod-shaped element can be designed in one piece with the membrane in an especially advantageous manner in the construction of the agitating or dispersing apparatus. However, other advantageous further developments of the connection of the rod-shaped to the membrane as part of a wall of the mixing chamber are conceivable. For example, this connection between rod and membrane can be formed in a hermetically sealing and power-transferring manner by a chemical reaction of the materials forming the two parts. A further development can also be considered in which the two parts enter a one-piece connection by a two-component injection molding process. Moreover, it is also conceivable to adhere the membrane to the rod or to provide the rod in a two-part manner with flanges that are adhered, welded or chemically connected to both sides of the membrane In any case, all the previously cited measures are suited for ensuring the hermetical seal of the membrane. In addition, a clamping connection that is tight with an appropriately high clamping force is possible between the rod-shaped element and the membrane.

Another advantageous embodiment is constituted by an agitating or dispersing apparatus in which the rod-shaped element is designed in several parts, preferably in one part on both sides of the membrane. Then, rod-shaped elements with different longitudinal sizes can be provided for such a design that can be subsequently arranged on the membrane so that mixing chambers with different longitudinal extensions, and thus also different volumes at a possibly unchanged cross section, can be realized.

Particularly economical solutions of the agitating or dispersing apparatus of the invention result if the rod-shaped element is designed and/or runs in a straight line, and in a further development the end of the rod shaped element facing the tool and running in a straight line opposite the diametrical plane of the agitating tool engages with play into a sufficiently large opening of the tool provided for this purpose. Such a transfer of power is completely sufficient, especially in the case of such apparatuses that can be used only for a limited time and that can even be provided in the extreme case as a disposable apparatus for one-time use, because the time of use is too short for any appreciable wear to be able to occur.

An advantageous further development is constituted by an agitating or dispersing apparatus in which the axis of rotation of the tool is vertically arranged and the rod-shaped element engages obliquely from the bottom toward the top or from the top toward the bottom into the tool since this facilitates a simple charging of the apparatus, the force of gravity can be utilized, and a rapid, reliable and erect positioning on a drive is possible. In another embodiment of the agitating or dispersing apparatus the tool can be detachably supported in a particularly advantageous manner on at least one edge shoulder inside the mixing chamber. This detachable support has the result that the tool can be lifted off of the shoulder and replaced. This makes it possible to use, e.g., a dispersing tool instead of a mixing tool, or instead of a dispersing tool a grinding tool or even no tool in a particular instance wherein the drive rod formed by the rod-shaped element is used as an agitating rod.

In another embodiment of the agitating or dispersing apparatus a detachable cover can be provided with advantage on the mixing chamber, which cover can be detached in order to fill in the material to be mixed and also in order to replace the tool. The cover does not necessarily have to be completely removed but can be provided, in order that it is not lost, with any type of additional connection, e.g., to the outer wall of the mixing chamber or with some similar loss prevention device.

In particular the cover, or another wall of the mixing chamber of the agitating or dispersing apparatus, can contain a pierceable membrane through which the material to be mixed or components to be added in or mixed in can be charged or even removed with the aid of a cannula and a needle. The membrane carrying the rod-shaped element can be provided as a pierceable membrane with a particular preference, especially in the instance in which the apparatus is intended to be used only once and is then disposed of (e.g., only one removal per cannula takes place so that the arranging of another membrane can be eliminated). Of course it is also possible to simultaneously provide several membranes as pierceable membranes.

A particularly good result is achieved in homogenizing and dispersing procedures with an agitating or dispersing apparatus in which the tool comprises an outer, fixed crown with teeth and/or cutting edges or the like and comprises a rotatable element arranged coaxially relative to the latter and also provided with teeth and/or cutting edges or the like, and wherein the rod-shaped element engages into a recess of the rotating element in the position of use since in this manner the rotating element of the tool can freely rotate and can prepare the material to be mixed in an optimal manner. The rotating element of the tool is preferably formed by at least two parts that can be separated from each other and are connected in the position of use in such a manner that they rotate in unison so that the engagement of the rod-shaped element driving the rotating part does not take place on the tool section but rather on a separate section of the rotating element facing the drive that can then also be individually designed and separately replaced.

In another embodiment of the agitating or dispersing apparatus a number of spheres or similar grinding elements to be placed into the mixing chamber can also be filled in as a tool between which the oblique driving rod extends so that as a result of its wobbling motion these grinding elements are put in motion and caused to mutually collide and accordingly comminute a material to be ground. In this instance these grinding elements or spheres practically form the tool driven by the wobbling rod.

It is advantageous in particular in the case of a mixing container or mixing chamber whose cross section is completely filled by a homogenizing or dispersing tool if projections, ribs or similar current-breaking devices are provided at least on the wall parallel to the axis, which devices advantageously function to fix the stationary crown of the tool against the rotary motion and engage for this purpose with at least one area of the tool, e.g., with grooves provided on the crown.

BRIEF DESCRIPTION OF THE DRAWINGS

The invention is explained in detail in the following drawing using exemplary embodiments.

DESCRIPTION OF THE PREFERRED
EMBODIMENTS OF THE PRESENT
INVENTION

Figure 1:
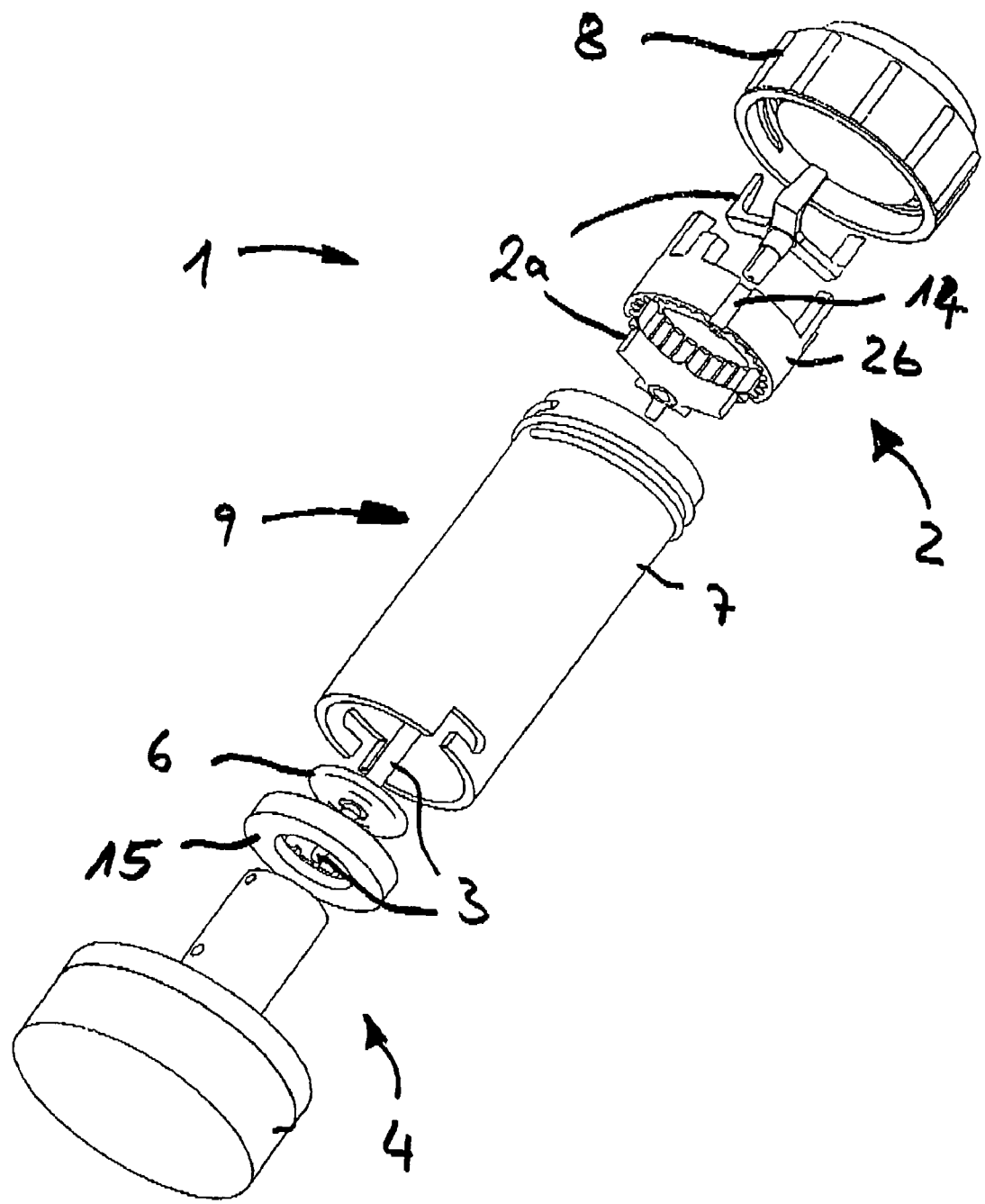
FIG. 1 shows a first embodiment of an agitating or dispersing apparatus in an exploded view.

FIG. 1 shows a dispersing apparatus, designated generally by the reference numeral 1, with a substantially cylindrical, tubular body 9 in whose interior a hermetically closed mixing chamber 5 (see FIG. 2) is formed. An agitating or dispersing tool 2 that can be driven about a central axis is located in this mixing chamber 5 which tool transfers the power of drive 4 by means of rod-shaped element 3. Drive 4, including a coupling, is located outside of mixing chamber 5 on the lower end of agitating or dispersing apparatus 1 and is attached thereto by fixing aids in the form of bayonet catches on body 9 of agitating or dispersing apparatus 1.

FIG. 1 also shows the rod-shaped element 3 connected to a membrane 6. Rod-shaped element 3 is fixed together with the membrane 6 at the entrance to mixing chamber 5 by annular closure piece 15 in such a manner that membrane 6 forms a part of wall 7 of mixing chamber 5, whose remaining part is formed by the walls of the cylindrical body and by cover 8 located on its end facing away from drive 4. Rod-shaped element 3 can be put in a wobbling motion by drive 4 and its end located in mixing chamber 5 then executes a circular movement during which membrane 6 also executes this movement in a pressing movement that deforms it in a certain manner, and during which this end of rod-shaped element 3 located in mixing chamber 5 attacks agitating or dispersing tool 2 eccentrically to its axis of rotation in mixing chamber 5.

Rotating element 2*a* of agitating or dispersing tool 2 is put in a circular motion by the eccentric attack and is then in a position to disperse material present in mixing chamber 5 in that cutting edges or teeth of rotating part 2*a* of agitating or dispersing tool 2 are moved past such cutting edges or teeth of static part 2*b* in the form of a crown during the rotation. Rotating part 2*a* of agitating or dispersing tool 2 is constructed in this instance from two multi-winged pieces that are connected in such a manner that they rotate in unison in the position of use. Rod-shaped element 3 attacks the piece of the side facing drive 4 whereas cutting edges are arranged on the other piece.

Cover 8, with includes a pierceable membrane, is provided for closing cylindrical body 9 and therewith also mixing chamber 5, as already mentioned. This cover can be attached with the aid of a threading on the outside of body 9 at the end of body 9 facing away from the drive.

Figure 2:
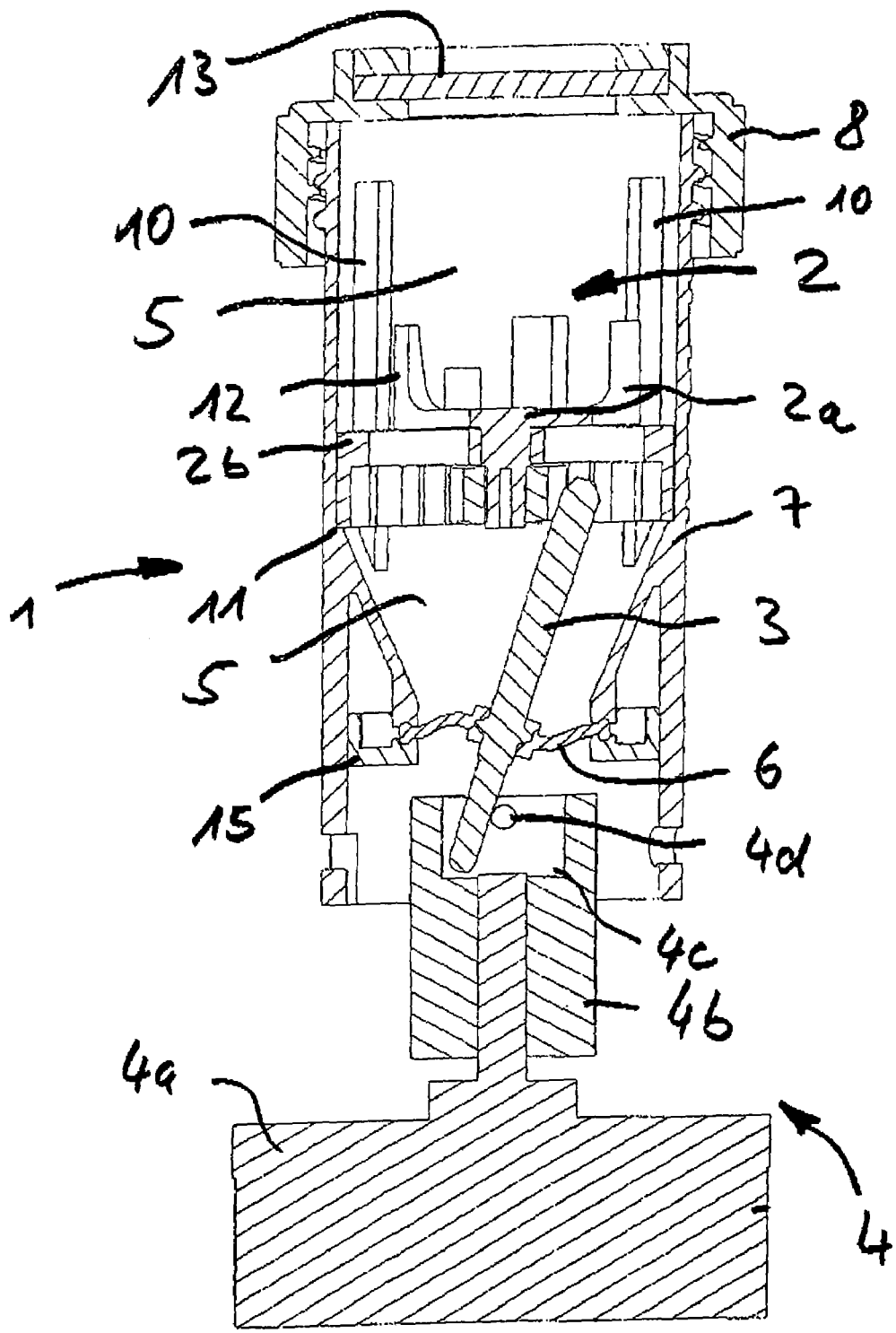
FIG. 2 shows a longitudinal section of a lateral view of the agitating or dispersing apparatus of FIG. 1 in an assembled state and in vertical position with the drive from below.

In FIG. 2 agitating or dispersing apparatus 1 can be recognized in the assembled state and set on drive 4. Drive 4 has a motor 4*a* with coupling 4*b* fastened axially on the motor shaft. This motor drives rod-shaped element 3, that forms a unit with membrane 6, with a rotary motion. This takes place in that the end of rod-shaped element 3 facing drive 4 is positioned in space 4*c* of coupling 4*b* where it is engaged by shaft 4*d* perpendicularly to the axis of rotation. The position of this shaft 4*d* and its diameter determine the diameter of the circular motion of the ends of rod-shaped element 3 and its angle to the drive shaft.

When driven, the ends of rod-shaped element 3, supported by membrane 6, execute a circular motion so that agitating or dispersing tool 2 is driven on the end of rod-shaped element 3 facing away from the drive. The deflection of membrane 6 is a consequence of the circular motion of the ends of wobbling, rod-shaped element 3, which deflection is also shown in FIG. 2, making it clear that it is subjected during operation to an operation of pressing that causes this deflection or deformation. Membrane 6 is clamped in place by annular closure piece 15 on the inner edge of wall 7 and relative to the free end of the wall-like limitation of mixing chamber 5 running out conically into mixing chamber 5. Groove-like recesses for receiving the thickened edge of membrane 6 are located on facing ends of these two parts.

Engaging or snap devices can also be arranged between closure piece 15 and a limitation of the mixing chamber (not shown). The end of rod-shaped element 3 located in mixing chamber 5 extends in a straight-line into mixing chamber 5 that widens out conically at the top. It extends obliquely from below with its upper end extending into the intermediate space between two wings of the lower part of rotor 2a of agitating or dispersing tool 2, and it rests on one of the wings and puts rotor 2a into rotation by its own circular motion.

Rotating element 2a of agitating or dispersing tool 2 rotates in this instance about its axis of rotation and is equipped on its upper part, that is, the end facing away from drive 4, with cutting edges 12. The rotation takes place in static crown 2b arranged coaxially to the rotating part. This crown is also provided with cutting edges, on which crown the upper part of rotating part 2a is supported and is connected to the lower part by the central shaft in such a manner that it rotates in unison with it. This crown 2b is detachably supported together with rotating part 2a as agitating or dispersing apparatus 2 on shoulder 11 inside mixing chamber 5 in such a manner that tool 2 can be entirely or partially replaced. It can be advantageous in order to counteract a movement of crown 2b in the direction of cover 8 caused by the rotating dynamics of rotating part 2a to additionally fix crown 2b in another suitable manner, e.g., by clamping (not shown).

Current-interrupting devices 10 are provided for limiting the mixing chamber that engages with an area of agitating or dispersing tool 2. Corresponding grooves 14 running in an axially parallel fashion are provided to this end on crown 2b to fix crown 2b against the rotary motion. The upper closure of agitating or dispersing tool 2 is formed by the cover 8 that is attached to wall 7 by a threading and is provided with pierceable membrane 13.

Figure 3:
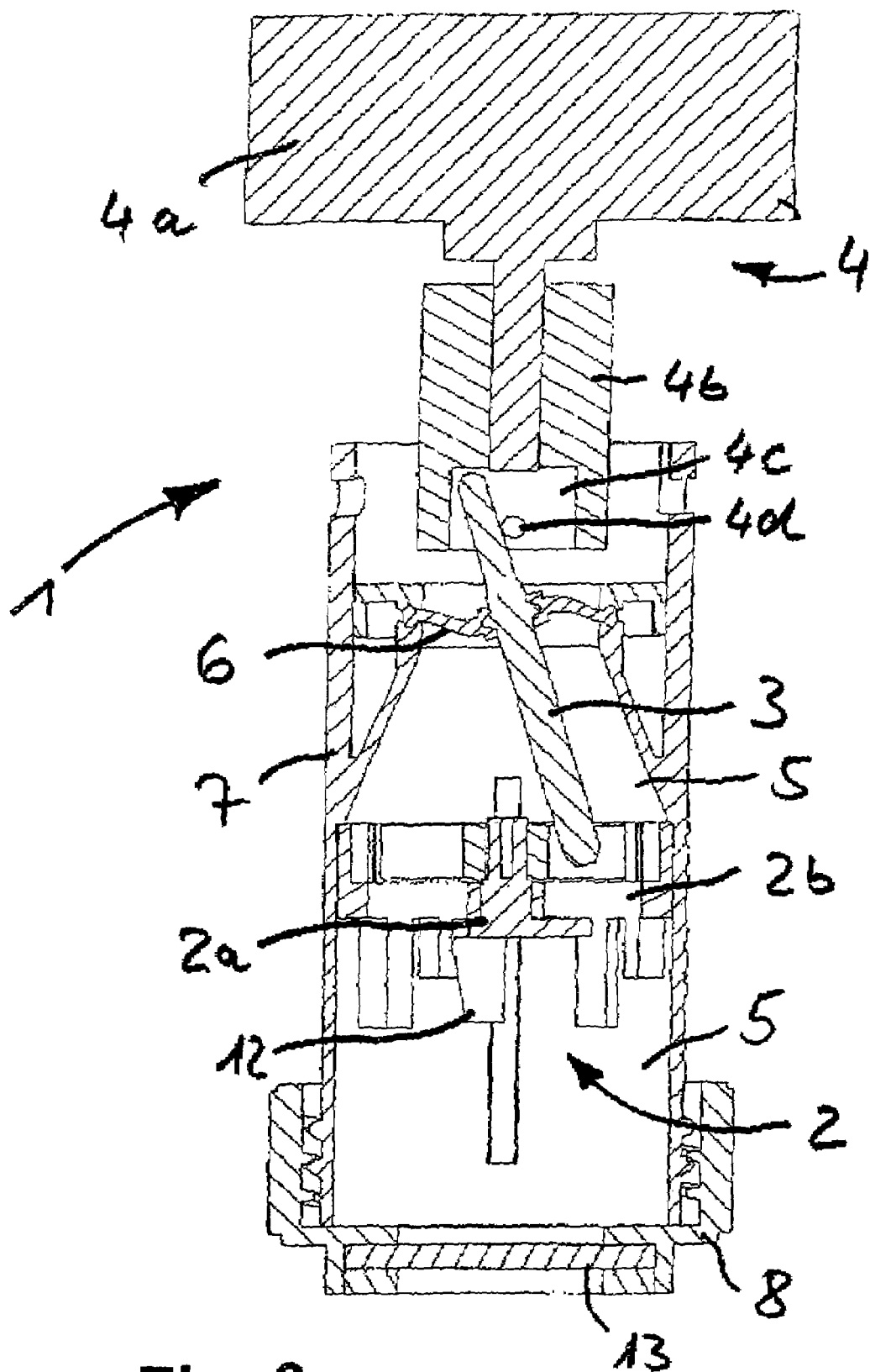
FIG. 3 shows a longitudinal section of a lateral view of another embodiment of the agitating or dispersing apparatus, namely, with the drive arranged at the top.

FIG. 3 shows an embodiment of agitating or dispersing apparatus 1 that corresponds in essential parts to those of FIG. 2; however, it stands on cover 8 in a vertical position and drive 4 of apparatus 1 is supplied from above. The entrainment of rod-shaped element 3 takes place via shaft 4d being arranged perpendicularly to the axis of rotation of drive 4, and the rod-shaped element engages under deflection of membrane 6 inside mixing chamber 5. In this embodiment, the rod-shaped element 3 extends obliquely from above and downwardly into the recess provided in rotating element 2a of agitating or dispersing tool 2 facing it. The upper part of rotor 2a is connected in such a manner that it rotates in unison, and it is provided with cutting edges 12.

Static element 2b of agitating or dispersing tool 2, that is crown 2b, is locked against a vertical shifting along the axis of rotation of the axis of rotation of rotor 2a in any suitable manner with wall 7 of mixing chamber 5. Cover 8 has pierceable membrane 13 arranged on it to cover and close a frontal access opening of cover 8, and form the lower closure of agitating or dispersing apparatus 1 and at the same time the surface upon which it stands.

Figure 4:
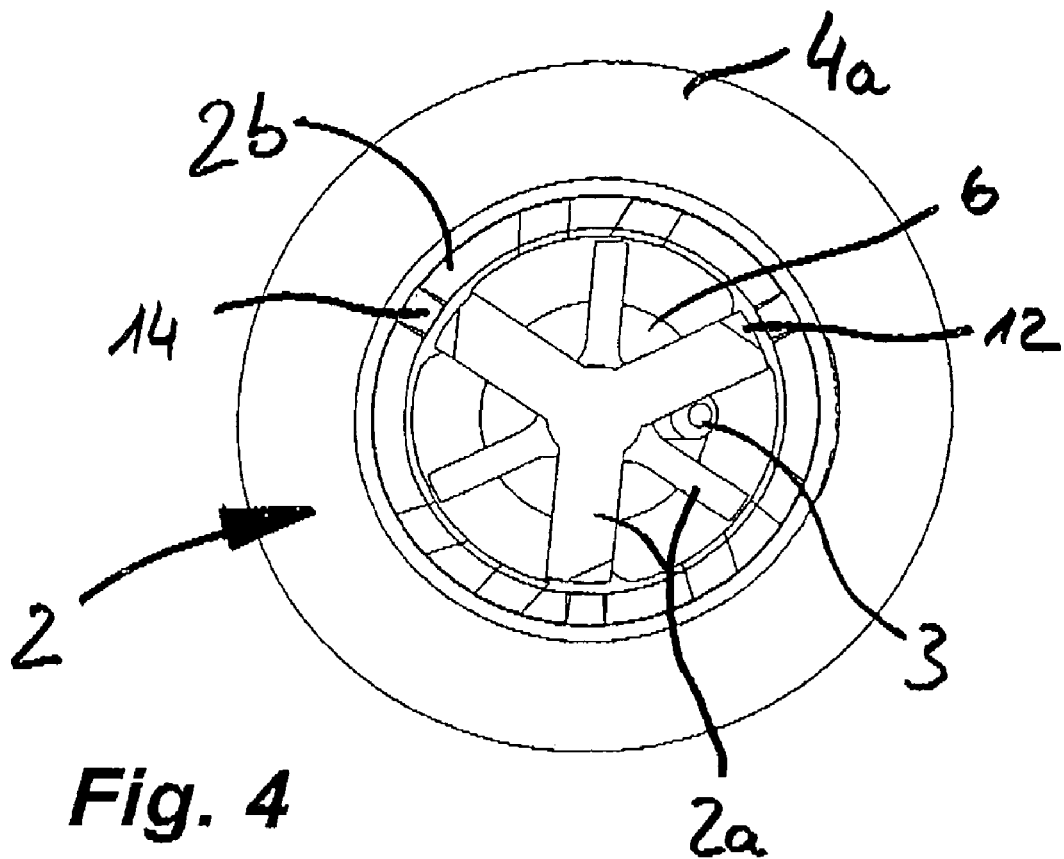
FIGS. 4 and 5 shows two frontal views of the cross section of a dispersing insert of the tool of the agitating or dispersing apparatus.
Figure 5:
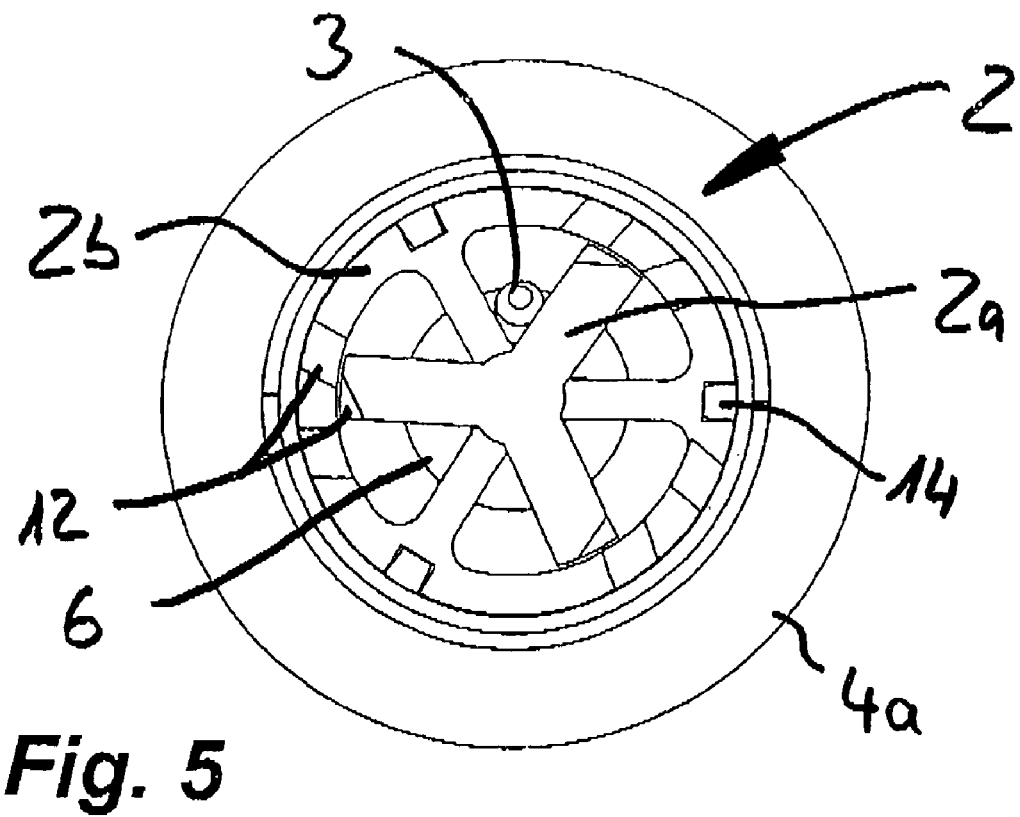

FIGS. 4 and 5 show frontal views of agitating or dispersing apparatus 1 with cover 8 removed from the top with two different positions of rotating part 2a inside static part 2b of agitating or dispersing tool 2 in engagement of rod-shaped element 3 supported on membrane 6 in the recess located between two wings of the part of rotating element 2a facing the drive.

FIG. 4 shows how rod-shaped element 3 engages a wing of lower part or rotating element 2a facing it during rotation that is clockwise for an observer and puts this lower part in rotation by engaging the wing, during which the lower part, by means of the connection, rotates in unison with the upper part of the rotating element, entrains the latter and causes it to rotate. The upper and the lower parts of rotating element 2a are designed with three wings. In the view of FIG. 4 the three wings of the upper part cover the three struts, running like spokes, of the static part, that is crown 2b, on which rotating part 2a is supported.

In FIG. 5, in which a rotation takes place that is counter-clockwise for an observer, the wings of the lower part of rotating element 2a are covered by the struts of the static part and the wings of the two parts of rotating element 2a do not necessarily always have to assume the same relative position to each other.

The previously described invention accordingly relates to an agitating or dispersing apparatus 1 with a hermetically closed mixing chamber 5, an agitating or dispersing tool 2 that can be driven in this mixing chamber 5 about a central axis and with a rod-shaped element 3 for transferring the power of a drive 4 onto this tool 2, and with such a drive 4 located outside of the mixing chamber 5.

In order to definitively prevent the exiting of material to be mixed from such an apparatus in the area of the drive, the following provisions are made for the apparatus: The rod-shaped element 3 is connected at the entrance into the mixing chamber 5 to a membrane 6 that forms part of a wall 7 of the mixing chamber 5, and the rod-shaped element 3 can be put in a wobbling motion by the drive 4 so that its end inside the mixing chamber 5 executes a circular motion, and the end of the rod-shaped element 3 located in the mixing chamber 5 attacks the agitating or dispersing tool 2 eccentrically to its axis of rotation.

In view of the aforesaid written description of the present invention, it will be readily understood by those persons skilled in the art that the present invention is susceptible of broad utility and application. Many embodiments and adaptations of the present invention other than those herein described, as well as many variations, modifications, and equivalent arrangements, will be apparent from or reasonably suggested by the present invention and the foregoing description thereof, without departing from the substance or scope of the present invention. Accordingly, while the present invention has been described herein in detail in relation to preferred embodiments, it is to be understood that this disclosure is only illustrative and exemplary of the present invention and is made merely for purposes of providing a full and enabling disclosure of the invention. The foregoing disclosure is not intended nor is to be construed to limit the present invention or otherwise to exclude any such other embodiments, adaptations, variations, modifications and equivalent arrangements, the present invention being limited only by the claims appended hereto and the equivalents thereof.

What is claimed is:

1. An agitating or dispersing apparatus (1) which includes a hermetically closed mixing chamber (5), an agitating or dispersing tool (2) that is driven in this mixing chamber (5) about a central axis by a rod-shaped element (3) for transferring the power of a drive (4) onto tool (2), and wherein drive (4) is located outside of the mixing chamber (5), wherein the rod-shaped element (3) is connected at the entrance into the mixing chamber (5) to a membrane (6) that is part of a wall (7) of the mixing chamber (5), wherein the rod-shaped element (3) is put in a wobbling motion by the drive (4) so that its end inside the mixing chamber (5) executes a circular motion, and wherein the end of the rod-shaped element (3) which is located in the mixing chamber (5) attacks the agitating or dispersing tool (2) eccentrically to its axis of rotation.

2. The agitating or dispersing apparatus according to claim 1, wherein the rod-shaped element (3) is designed in one piece with the membrane (6).

3. The agitating or dispersing apparatus according to claim 1, wherein the rod-shaped element (3) and the membrane (6) are connected by a chemical reaction of their materials.

4. The agitating or dispersing apparatus according to claim 1, wherein the rod-shaped element (3) is connected to the membrane (6) by an adhesive connection.

5. The agitating or dispersing apparatus according to claim 1, wherein the rod-shaped element (3) is formed in several parts within one part on each side of the membrane (6).

6. The agitating or dispersing apparatus according to claim 1, wherein the rod-shaped element (3) extends in a straight line.

7. The agitating or dispersing apparatus according to claim 1, wherein the end of the rod-shaped element (3) facing the tool (2) engages with play into an opening of the tool (2).

8. The agitating or dispersing apparatus according to claim 1, wherein the axis of rotation of the tool (2) is arranged vertically and the rod-shaped element (3) extends obliquely from the bottom upwardly or from the top downwardly into the tool (2).

9. The agitating or dispersing apparatus according to claim 1, wherein the tool (2) is detachably supported on at least one edge shoulder (11) inside the mixing chamber (5).

10. The agitating or dispersing apparatus according to claim 1, wherein a detachable cover 8 is provided on the mixing chamber (5).

11. The agitating or dispersing apparatus according to claim 1, wherein a pierceable membrane (13) is arranged in one of the walls (7) provided in the cover (8) of the mixing chamber.

12. The agitating or dispersing apparatus according to claim 1, wherein the membrane (6) carrying the rod-shaped element (3) is a pierceable membrane.

13. The agitating or dispersing apparatus according to claim 1, wherein the tool (2) comprises an outer, fixed crown (2b) with cutting edges (12) and comprises a rotatable element (2a) arranged coaxially relative to the crown and also being provided with teeth (12), and the rod-shaped element (3) engages into a recess of the rotating element (2a).

14. The agitating or dispersing apparatus according to claim 13, characterized in that the rotating element (2a) of the tool (2) is formed by at least two parts that can be separated from each other and are connected to rotate in unison.

15. The agitating or dispersing apparatus according to claim 1, wherein the tool (2) is formed by a number of spheres positioned in the mixing chamber 5.

16. The agitating or dispersing apparatus according to claim 1, wherein current-breaking devices (10) are provided at least on the wall (7) parallel to the axis.

17. The agitating or dispersing apparatus according to claim 16, characterized in that current-breaking devices (10) engage with at least one area of the tool (2).

18. The agitating or dispersing apparatus according to claim 1, wherein the rod-shaped element (3) is connected to the membrane (6) by a flange connection.

19. The agitating or dispersing apparatus according to claim 1, wherein the rod-shaped element (3) is connected to the membrane (6) by a welding connection.

20. The agitating or dispersing apparatus according to claim 1, wherein the rod-shaped element (3) is connected to the membrane (6) by a clamping connection.

* * * * *